United States Patent [19]

Ingraffea

[11] Patent Number: 4,481,826
[45] Date of Patent: Nov. 13, 1984

[54] HAND HELD, DIRECT READING, FULLY MECHANICAL FRACTURE LOADING DEVICE FOR SHORT ROD/BAR SPECIMENS

[75] Inventor: Anthony R. Ingraffea, Ithaca, N.Y.

[73] Assignee: Cornell Research Foundation, Inc., Ithaca, N.Y.

[21] Appl. No.: 463,358

[22] Filed: Feb. 2, 1983

[51] Int. Cl.³ ............................................. G01N 19/08
[52] U.S. Cl. ................................................... 73/799
[58] Field of Search .................. 73/799, 862.62, 818; 81/302

[56] References Cited

U.S. PATENT DOCUMENTS 1,557,341 10/1925 Scalbom .................. 73/862.62 X
4,066,082 1/1978 Arcan et al. .................. 73/818 X
4,198,870 4/1980 Barker et al. .................. 73/799

*Primary Examiner*—Jerry W. Myracle
*Attorney, Agent, or Firm*—Sughrue, Mion, Zinn, Macpeak, and Seas

[57] ABSTRACT

Expandable jaws comprise lever arms pivoted together at their base and forming a bifurcated Y-shaped assembly which acts by force application to fracture a specimen. The force is applied through and measured by deflection of a force gauge U-spring having one side fixed to one of the lever arms remote from the specimen and the other cable connected via a threaded shaft and knob to the other lever arm. A dial reads directly the force required to effect fracture toughness, fatigue crack, growth resistance or stress corrosion crack growth resistance of slotted short rod/bar specimens.

7 Claims, 3 Drawing Figures

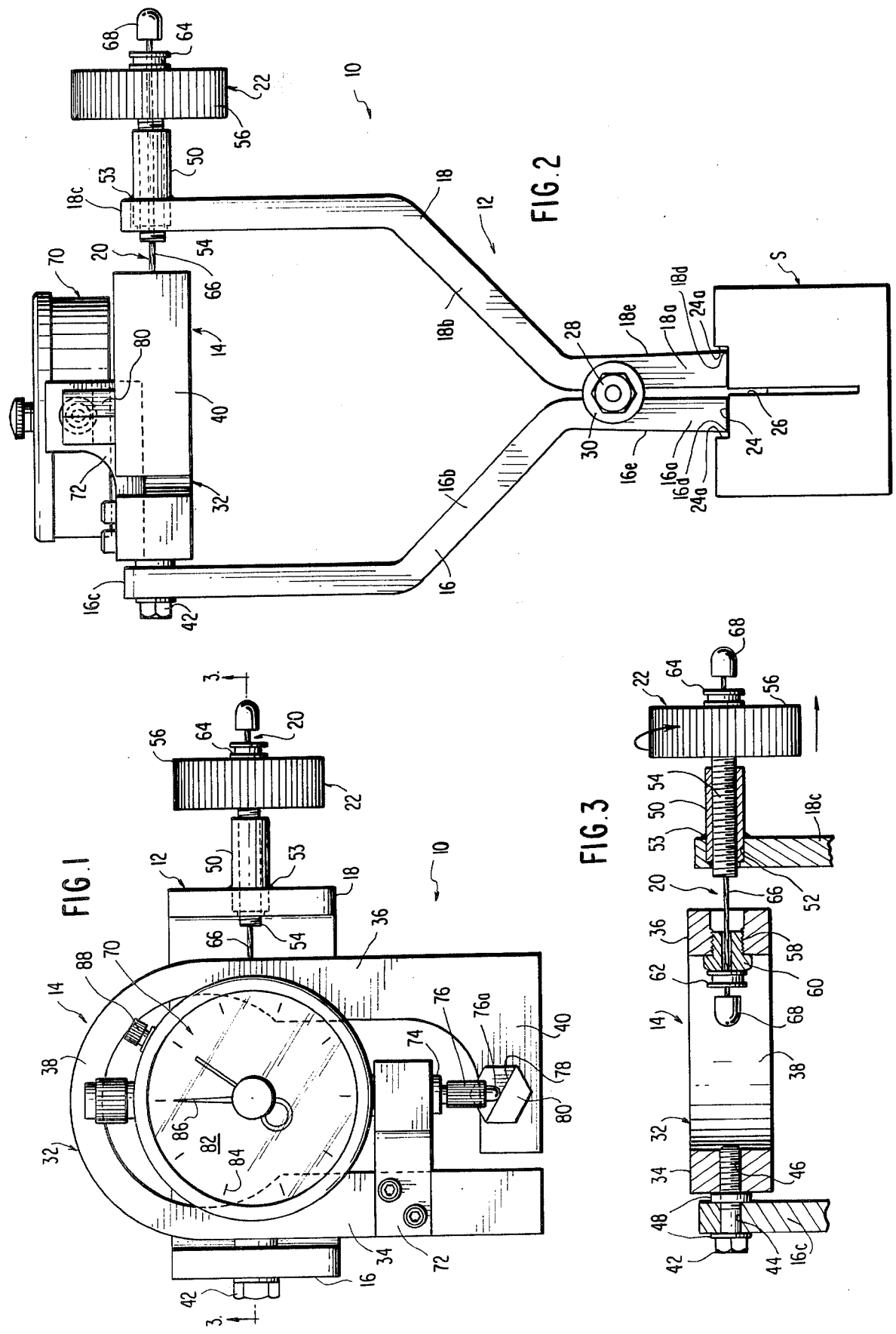

HAND HELD, DIRECT READING, FULLY MECHANICAL FRACTURE LOADING DEVICE FOR SHORT ROD/BAR SPECIMENS

BACKGROUND OF THE INVENTION

1. Field of the Invention

This invention relates to the testing of materials for fracture toughness, fatigue crack growth resistance and stress corrosion crack growth resistance, and more particularly, to a simple portable hand held loading device which is fully mechanical and which provides direct reading of fracture toughness using the short rod/bar specimen geometry.

2. Description of the Prior Art

Fracture toughness, $K_{Ic}$, is an intrinsic material property and is a measure of the energy required to create new surface area in a material. Fracture toughness measurements can be made for a wide range of rock types for example. As a measure of energy comminution, fracture toughness might be used for more sensitive predictions of tunnel boring machines (TBM) performance than are possible with other index measures in current use. Such testing is quite often done with specimens of short rod/bar geometry which include a machine slot where crack growth initiates from the root of the slot. Under test, load is applied to the specimen which tends to increase the machine slot width. Material testing machines conventionally involve arms that fix to parts of the specimen and which, when energized, move apart to widen the specimen slot, thus effecting fracture of the specimen.

Fairly sophisticated machines have been developed for loading of a slotted specimen and for measuring the fracture toughness, fatigue crack growth resistance, or stress corrosion crack growth resistance of that specimen. U.S. Pat. No. 4,075,884 issuing Feb. 28, 1978, is illustrative of one machine of the hydraulic type involving a thin pressure bag installed within the slotted portion of the specimen and expanded by application of hydraulic fluid to produce a desired specimen loading. By measuring the hydraulic pressure at fracture, a determination of the load applied to the specimen is ascertained. Such materials testing machine is complicated and has all the attendant problems of dealing with a liquid under pressure, such as loss of seal and the requirement to transmit the hydraulic fluid to and from the pressure bag.

U.S. Pat. No. 4,198,870 issuing Apr. 22, 1980 describes a second type of sophisticated machine wherein a pair of fixed outer arms at their upper ends function as a pivot for a rigid center arm with each arm arranged to mount a grip coupled below the pivot via opposed grooves to a short rod, short bar or other fracture test specimen. The machine is further characterized by a motor and screw means turning in a threaded collar for pivoting the center arm relative to the side arms. Spring gauge means secured to the middle arm senses flexure and indicates the load forces required to achieve fracture. While this machine operates satisfactorily to adequately measure the applied force, a motor is required to provide the applied force, the stress on the test specimen is sensed separately from the force application means, and the mechanism does not lend itself to portability and hand held use.

It is, therefore, a primary object of the present invention to provide an improved hand held, direct reading, fracture loading device for short rod/bar specimens which employs a mechanical force gauge to measure directly the maximum load reading required by the specimen geometry and in which the load applied to the specimen is applied through the force gauge itself.

It is a further object of the present invention to provide such a fracture toughness measuring device which is actuated solely by hand turning of a knob borne by the unit and which eliminates complex electronic or hydraulic components characterizing prior machines.

SUMMARY OF THE INVENTION

A fully mechanical, hand held, portably direct reading, fracture loading device for short rod/bar specimens and the like comprises expandable jaws constituting a pair of lever arms pivotably connected intermediate of their ends, having ends to one side of the pivot engaging opposed sides of a slotted test specimen such that when those ends of the lever arms are pivoted apart, the test specimen splits. A mechanical force gauge including a spring flexure member is interposed between the ends of the lever arms to the opposite side of the pivot.

Means are provided for applying a force for drawing the ends of the lever arms bearing the mechanical force gauge towards each other through the spring flexure member such that flexure of the spring flexure member is a measure of the load applied to the test specimen through the lever arms to effect fracture thereof.

The mechanical force gauge spring flexure member may be U-shaped including opposed, generally parallel flexible arms with one of the spring flexure member arms fixedly mounted to one of the lever arms and wherein the means for applying the force for drawing together the ends of the lever arms bearing the mechanical force gauge comprise a flexible cable spanning between the other of the spring flexure member flexible arms and the other lever arm. Means are provided for tensioning the cable to cause the lever arms to pivot with the cable pulling the U-shaped flexure member flexible arms apart under the applied tension.

The lever arms preferably take the form of expandable jaws of Y-shape configuration, being pivotably connected at a base portion thereof with the mechanical force gauge interposed between the bifurcated portion of the lever arms remote from the base portion. A force application knob is rotatably mounted to the other lever arm, and means are provided for operatively connecting the rotatable knob to the cable for tensioning the cable connecting one spring flexure member flexible arm to the lever arm bearing the rotatable knob.

The lever arm bearing the rotatable knob may fixedly mount a sleeve which threadably receives a hollow shaft fixedly mounting the force applying knob. The threaded sleeve projects outwardly of the side of the lever arm perpendicular to the longitudinal axis of the lever arm and to the outside of the lever arm. Holes borne by the threaded shaft, the threaded sleeve, the one lever arm and the free flexible arm of the spring flexure member carry the cable with the cable stops at opposite ends of the cable such that by rotation of the knob, the threaded shaft and the knob move axially outwardly away from the threaded sleeve and the one lever arm. When the stops abut the knob and the free flexible arm of the spring flexure member, force is applied to the lever arms tending to pivot the bifurcated ends bearing the force gauge towards each other resisted by the deflection of the free arm of the force gauge spring flexure member away from the fixed arm thereof in proportion to the force applied through the lever arms to the specimen tending to fracture the same. The faces of the lever arms at their ends in contact with the specimen are preferably slightly tapered to insure line contact between the ends of the lever arms and opposed groove faces within the specimen for accurate fracture force application to the specimen. A direct reading gauge dial is mounted by means of a support fixed to the arm of the spring flexure member fixedly mounted to the one lever arm. The gauge bears a plunger projecting through the gauge dial mount with its outboard end contacting a follower surface operatively fixed to the free arm of the spring flexure member; whereby, flexure of the spring flexure member and movement of the follower surface permits the plunger to follow the movement. The gauge includes a rotatable indicator hand operatively coupled to the plunger for indicating the extent of movement of the plunger and thus the applied fracture force exerted on the specimen.

BRIEF DESCRIPTION OF THE DRAWINGS

FIG. 1 is a top plan view of the portable direct reading fracture loading device for short rod/bar specimens forming a perferred embodiment of the present invention.

FIG. 2 is a side elevational view thereof.

FIG. 3 is a vertical sectional view taken about line 3—3 of FIG. 1.

DESCRIPTION OF THE PREFERRED EMBODIMENT

Referring to the drawings, the hand held, portable, direct reading, fracture loading device in one form is indicated generally at 10 and comprises principally: expandable jaws indicated generally at 12, a mechanical force gauge indicated generally at 14 which is interposed between the bifurcated ends of lever arms 16 and 18 defining the expandable jaws, a cable assembly indicated generally at 20 for coupling the bifurcated ends of lever arms 16 and 18 together through the mechanical force gauge 14 for applying force to the specimen for fracturing the same, and a rotatable knob 22 for effecting that force application through cable assembly 20.

The lever arms 16 and 18 are of heavy gauge steel plate, being rigid and of rectangular cross section. Arm 16 includes integrally: a short length base portion 16a, an oblique divergent portion 16b, and a straight bifurcating portion 16c being generally in line with base portion 16a but laterally offset therefrom. Lever arm 18 is similarly provided with an integral base portion 18a, a diverging connecting portion 18b and a straight bifurcating portion 18c. Lever arms 16 and 18 are mirror images of each other. It is preferred that the unit provide force amplification for rupturing or breaking a specimen S in half. The specimen S may be of block form having a central machined groove 24 within one end thereof within which are positioned ends 16a, 18a of the expandable jaws 12.

Additionally, the specimen S includes a narrow slot 26 which extends from groove 24 axially or centrally through the specimen to a given distance. Slot 26 may be formed by sawing from opposite sides such that the slot 26 is deeper near the outside of the specimen and shallower at the center thereof with inclined slot portions meeting at the center of the specimen, in accordance with conventional testing practice.

The lever arms 16 and 18 are pivotably connected within their base portions 16a, 18a by means of pivot pin or bolt 28 and through ring keepers as at 30 on opposite sides of the expandable jaws. Alternate means may be provided for pivoting the lever arms together at their bifurcated ends causing spreading at the base portion ends contacting the specimen. The applied force functioning to fracture the specimen is amplified by the inverse ratio of the distances between the pivot axis of the expandable jaws 12 and the line contact with the specimen as defined by edges 16d and 18d for expandable jaws 12 meeting opposed groove faces 24a, as compared to the distance from the same pivot axis defined by pin 28 and the point of force application between bifurcated portions 16c and 18c of the lever arms tending to draw those lever arm portions together. While the outside faces 16e and 18e of the lever arm base portions 16a and 18a appear to be parallel to each other, they incline slightly downwardly and outwardly from the pivot axis towards contact edges 16d, 18d, respectively, of these lever arms. The purpose is to insure that the lever arms contact the specimen only at the edges 16d, 18d of these members so that there is single line contact between the fracture thoughness measuring device and the specimen to each side of the desired fracture plane.

The mechanical force gauge 14 comprises a very essential element of the hand held direct reading portable fracture toughness measuring device 10. The mechanical force gauge 14 is a commercially available item. In the illustrated embodiment, it may comprise a Model X force gauge manufactured by W. C. Dillon Company. Its principal component is a spring flexure member indicated generally at 32 comprising a generally U-shaped spring metal bar including opposite generally parallel flexible arms 34, 36 joined by an integral base 38 with arm 36 terminating in a transverse head 40 which extends laterally across the open end of the U terminating short of the first flexible arm 34. The lateral width of the spring flexure member 32 is less than the width of the opening between lever arm bifurcated portions 16c and 18c, and this member is interposed therebetween. One spring flexure member flexible arm 34 is fixedly mounted to lever arm 16 by being bolted to lever arm portion 16c. In that respect, a gauge attachment bolt 42 extends through hole 44 and may be threaded within tapped hole 46 within lever arm portion 16c and the flexible arm 34 of the spring flexure member 32, respectively. Washers 48 are interposed between the bolt head 42a and lever arm portion 16c and between lever arm portion 16c and the spring flexure member 32. Arm 36 of the spring flexure member is essentially a free flexible arm, that is, it may flex freely relative to the other arm and is not fixedly coupled to lever arm 18 of expandable jaws 12. However, a mechanical connection is made through the force gauge 14 from arm portion 18c of lever arm 18 to arm portion 16c of lever arm 16.

As may be appreciated, it is only by causing the lever arms portions 16c and portion 18c to pivot towards each other, that the base portions 16a and 18a pivot away from each other below the expandable jaw pivot axis, thus a fracture or load force is applied to the specimen to achieve fracture along the fracture plane as predescribed by saw cut slot 26. A metal sleeve 50 is fixedly mounted to lever arm portion 18c and extends perpendicular to its longitudinal axis. A hole may be drilled as at 52 within lever arm portion 18c with the sleeve 50 being of such a diameter and length so that a portion projects the length of hole 52, which may be welded thereto as at 53. The sleeve 50 is threaded internally so as to receive an external threaded shaft 54. A hand ajustment circular metal knob 56 is fixed coaxially to the end of shaft 54 such that by rotation of the knob 56, the threaded shaft 54 moves axially within the sleeve 50 and relative to lever arm portion 18c moving knob 56 towards or away from lever arm portion 18c. Arm 36 of the spring flexure member 32 is tapped as at 58 and threadably receives a bearing bolt 60, the bearing bolt carrying a first anti-friction spacer 62 coaxial therewith.

Further, to the side of knob 56 opposite shaft 54 is carried a second anti-friction spacer 64. The spacers 62 and 64, the bearing bolt 60, sleeve 50, threaded shaft 54 and knob 56 carry aligned holes, through all of which freely passes a flexible cable 66. The cable 66 is of relatively short predetermined length and terminates at its ends in radially enlarged cable stops 68.

As may be appreciated, rotation of knob 56, whose outer surface is knurled to facilitate manual gripping, causes the threaded shaft 54 to move axially within sleeve 50. FIG. 3, as indicated by the arrows, by rotation of the knob counterclockwise when viewed from the right, shaft 54 will move axially to the right to the extent where stop 68 engages anti-friction spacer 62 to the left of spring flexure force gauge flexure member arm 36, while the stop 68 at the opposite end of cable 66 engages spacer 64. At this point, further rotation of knob 56 in a counterclockwise direction tensions cable 66 and forces the lever arm portions 16c and 18c to move towards each other resisted by the resiliency of the spring flexure member 32. Flexible arm 36 therefore tends to move away from flexible arm 34 of the force gauge with the deflection of one flexible arm with respect to the other being a measure of the force applied by knob 56 to the expandable jaws 12 tending to fracture the specimen S.

The flexure of spring flexure member 32 is a measure of the fracture force applied to the specimen, which is directly indicated by the indicator dial 70 forming a part of that instrument. In that respect, a gauge dial mount bar 72 extends fixedly at right angles to arm 34 of the spring flexure member upon which mounts by way of bushing 74 the dial indicator 70. The instrument carries a spring biased plunger as at 76 which projects through the bushing 74 and whose outboard ends 76a contact inclined face 78 of a follower 80 projecting outwardly from head 40 of the spring flexure member 32 and fixedly mounted thereto. The indicator dial 70 bears a dial face 82 upon which are appropriate indicia 84 constituting, for example, a fracture toughness scale. A needle 86 mounted for rotation about one end at the center of dial face 82 and being operatively driven by plunger 76 indicates the maximum load reading required to effect fracture of the specimen as the load is increased by rotation of knob 56, previously described.

The instrument includes a calibration knob 88 or other means for calibrating the indicator dial, that is, to provide a zero setting absent applied force through knob rotation prior to force application as contact edges 16d, 18d of the lever arms.

In operation, with the base portions 16a, 18a of the expandable jaws 12 inserted within the groove 24 of specimen S, the knob 56 is rotated to the point where contact is made between edges 16d, 18d and groove faces 24a of the specimen itself or with plates which may be welded or otherwise adhesively affixed to the surface of the specimen to opposite sides of the sides of the fracture plane. Indicator dial 70 is then set to zero, if necessary, by way of calibrating knob 88. Subsequently, as may be appreciated, simply by hand turning of knob 56 counterclockwise, a fracture force is applied, the machine employing no electronic or hydraulic components. The squeezing force at the knob end of the device applies a fracture force measured by the force gauge 14 and amplified by mechanical advantage to the specimen itself. By combining the device's mechanical advantage and the calibration constant of the short rod/bar specimen geometry of sample specimen S, the dial 84 of the force gauge 14 can be calibrated to give a direct read out of $K_{Ic}$. Alternatively, simple monographs for each specimen geometry can be entered with the gauge reading corrected for mechanical advantage.

Distinct advantages result from the utilization of the combined fracture machine and measuring device. The device is inexpensive to build, cheap to maintain and calibration costs are essentially non-existent. The device is hand held, very simple in structure, and requires no electrical or hydraulic power supply, and thus is universally applicable. The device weighs only a few pounds and can fit in the corner of a brief case, making it a highly portable unit. The test set up can be effected within a few seconds. The unit permits access to all surfaces of the test specimens for attachment of additional measurement transducers since the corners or edges 16d, 18d of the base portions 16a and 18a of the expandable jaws provide minimum interference with access to the specimen itself. This permits a set of calibrated clamps to be applied to surfaces to the right and left of the jaw base portion 16a, 18a to provide clamping parallel to the fracture plane and to opposite sides thereof. By use of these additional clamps, there is virtually eliminated any premature undesirable specimen failure, all facilitated by the simplicity of the instant unit and permitting ready access to the major portions of the surface of the specimen under test. While the force gauge is shown as being perpendicular with the plane of the unit itself and to the longitudinal axis, it can be readily rotated via the gauge attachment bolt 42 so that the spring flexure member 32 is essentially coplanar to the plane of jaws 12, facilitating reading from the side of the specimen being tested, rather than to the top of the same.

While the invention has been particularly shown and described with reference to a preferred embodiment thereof, it will be understood by those skilled in the art that various changes in form and details may be made therein without departing from the spirit and scope of the invention.

What is claimed is:

1. A fully mechanical, hand held, portable, direct reading fracture loading device for short rod/bar specimens and the like, said device comprising:

force application expandable jaws constituting a pair of lever arms pivotably connected intermediate of their ends and having ends to one side of the pivot point engaging opposite sides of a slotted test specimen such that when the ends of the lever arms in contact with the specimen are pivoted apart, the test specimen splits, a mechanical force gauge including a spring flexure member interposed between the ends of the lever arms remote from the specimen, and means for applying a mechanical force for drawing the ends of the lever arms bearing the mechanical force gauge towards each other through said spring flexure member such that flexure of said spring flexure member is a direct measure of the load applied to the test specimen through the lever arms to effect fracture thereof.

2. The device as claimed in claim 1, wherein said mechanical force gauge spring flexure member is of generally U-shaped configuration including opposed, generally parallel flexible arms joined through a base, one of said spring flexure arms being fixedly mounted to one of said lever arms, and wherein said means for applying the mechanical force for drawing the ends of the lever arms bearing the mechanical force gauge towards each other through the spring flexure member comprises a flexible cable joining the other of the spring flexure members flexible arms and the other lever arm, and means for tensioning the cable to cause the lever arms to pivot and for causing the cable to pull the U-shaped flexure member flexible arms apart under the applied cable tension.

3. The device as claimed in claim 2, wherein said expandable jaws are of Y-shaped configuration, each arm including a straight base portion, a diverging connection portion and a bifurcating force gauge mounting portion which is generally parallel to the base portion, the lever arms being mirror images of each other and wherein said lever arms are pivotably connected at their base portions, the mechanical force gauge is interposed between the bifurcated portions of the lever arms remote from the base portion, a force application knob is rotatably mounted to the other lever arm and means are provided for operatively connecting the rotatable knob to the cable for tensioning the cable through one flexible arm of the spring flexure member.

4. The device as claimed in claim 3, wherein said lever arm bearing said rotatable knob comprises a hollow sleeve, a hollow shaft is threadably mounted within said sleeve and coaxial therewith, said rotatable knob is fixedly mounted to the end of said hollow shaft remote from said force gauge spring flexure member, aligned holes are provided within the threaded shaft, the threaded sleeve, said one lever arm and the flexible arm of said spring flexure member, said cable is slidably received by said holes, radially enlarged stops are fixed to the ends of said cable, and wherein said cable is of a length such that upon rotation of the knob such that the threaded shaft causes the knob to move axially outwardly away from the threaded sleeve and said one lever arm, said stops abut the knob and said free flexible arm of said spring flexure member, force is mechanically applied to the lever arms tending to pivot the bifurcating ends bearing said force gauge towards each other, resisted by the deflection of the force gauge spring flexure member in direct proportion to the force applied, with the ends of the lever arms in contact with the specimen moving apart to fracture the specimen along the predetermined fracture plane.

5. The device as claimed in claim 4, wherein the faces of the lever arms at their ends in contact with the specimen are inclined from the pivot axis outwardly to insure line contact between the ends of the lever arms and opposed groove faces within the specimen for accurate fracture force application to the specimen.

6. The device as claimed in claim 1, wherein the faces of the lever arms at their ends in contact with the specimen are inclined from the pivot axis outwardly to insure line contact between the ends of the lever arms and opposed groove faces within the specimen for accurate fracture force application to the specimen.

7. The device as claimed in claim 5, wherein a direct reading gauge dial is mounted to the flexible arm of the spring flexure member fixedly mounted to said one lever arm, said gauge bears a plunger projecting through the gauge dial mount, and a follower surface is operatively fixed to the free arm of the spring flexture member and in the path of the plunger for contact therewith; whereby, flexure of said spring flexure member and movement of the follower causes the plunger to follow the follower movement, and wherein said gauge includes a movable indicator element operatively coupled to the plunger such that movement of the indicator element indicates the extent of movement of the plunger and thus the applied fracture force exerted on the specimen.

* * * * *